(12) United States Patent
Krueger

(10) Patent No.: US 7,182,228 B2
(45) Date of Patent: Feb. 27, 2007

(54) CARTRIDGE WITH CONNECTION FOR A PUMP-DRIVE AND FLUID HANDLING SYSTEM

(75) Inventor: Andreas Krueger, Bubenreuth (DE)

(73) Assignees: Siemens Aktiengesellschaft, Munich (DE); directif GmbH, Erlangen (DE)

( * ) Notice: Subject to any disclaimer, the term of this patent is extended or adjusted under 35 U.S.C. 154(b) by 381 days.

(21) Appl. No.: 10/672,219

(22) Filed: Sep. 26, 2003

(65) Prior Publication Data

US 2004/0124214 A1    Jul. 1, 2004

(30) Foreign Application Priority Data

Sep. 26, 2002   (DE)   ................ 102 44 960

(51) Int. Cl.
*B67D 5/42* (2006.01)
(52) U.S. Cl. .............. 222/386; 222/326; 222/333; 222/340
(58) Field of Classification Search .......... 222/326, 222/340, 386, 386.5, 333; 604/193, 187, 604/218
See application file for complete search history.

(56) References Cited

U.S. PATENT DOCUMENTS

| | | | | |
|---|---|---|---|---|
| 2,702,547 A * | 2/1955 | Glass | .................. | 604/155 |
| 3,253,592 A * | 5/1966 | Von Pechmann | ............ | 604/222 |
| 3,291,128 A * | 12/1966 | O'Neil | .................. | 604/125 |
| 3,323,682 A * | 6/1967 | Creighton, Jr. et al. | ........ | 222/94 |
| 3,967,759 A * | 7/1976 | Baldwin et al. | ............. | 222/129 |
| 3,986,645 A * | 10/1976 | Baldwin et al. | ............. | 222/386 |
| 4,057,050 A * | 11/1977 | Sarstedt | .................. | 600/578 |
| 4,185,628 A * | 1/1980 | Kopfer | .................. | 604/82 |
| 4,673,396 A * | 6/1987 | Urbaniak | ................ | 604/211 |
| 4,869,403 A * | 9/1989 | Bruning | .................. | 222/327 |
| 4,890,627 A * | 1/1990 | Haber et al. | ................ | 600/578 |
| 5,238,003 A * | 8/1993 | Baidwan et al. | ............ | 600/578 |
| 5,499,751 A * | 3/1996 | Meyer | ................... | 222/386 |

FOREIGN PATENT DOCUMENTS

| | | |
|---|---|---|
| DE | 239 539 | 10/1986 |
| DE | 239 540 | 10/1986 |
| DE | 299 156 | 4/1992 |
| DE | OS 1956 52 272 | 8/1998 |
| DE | OS 197 08 151 | 9/1998 |
| DE | OS 198 26 065 | 12/1999 |

(Continued)

*Primary Examiner*—Frederick C. Nicolas
(74) *Attorney, Agent, or Firm*—Schiff Hardin LLP

(57) ABSTRACT

In a cartridge for a fluid, as well as a system for handling a fluid using such a cartridge, the cartridge has a tank shaped as a cylinder with an opening to admit and discharge the fluid, as well as a piston that can be moved forward and/or back in the tank in order to pump the fluid in or out through the opening. The piston has a connection element that can be connected with an actuator in order to move the piston forward and/or back. The connection element and the actuator are adapted to one another such that the connection is automatically closed in a first longitudinal section of the tank, given movement of the piston in the longitudinal direction and is automatically released again given movement in the opposite direction, and the connection remains closed in a second longitudinal section of the tank given movement of the piston into this second longitudinal section.

13 Claims, 2 Drawing Sheets

FOREIGN PATENT DOCUMENTS

| | | |
|---|---|---|
| EP | 0 155 087 | 2/1985 |
| EP | 0 181 957 | 5/1986 |
| EP | 0 226 867 | 7/1987 |
| EP | 0 600 580 | 8/1993 |
| EP | 0 734 769 | 10/1996 |
| GB | 1 525 829 | 9/1978 |

* cited by examiner

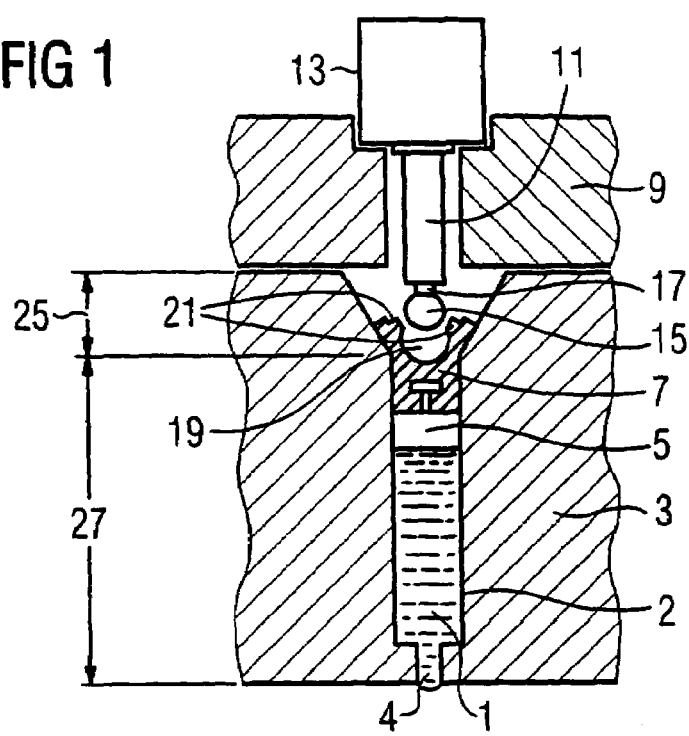
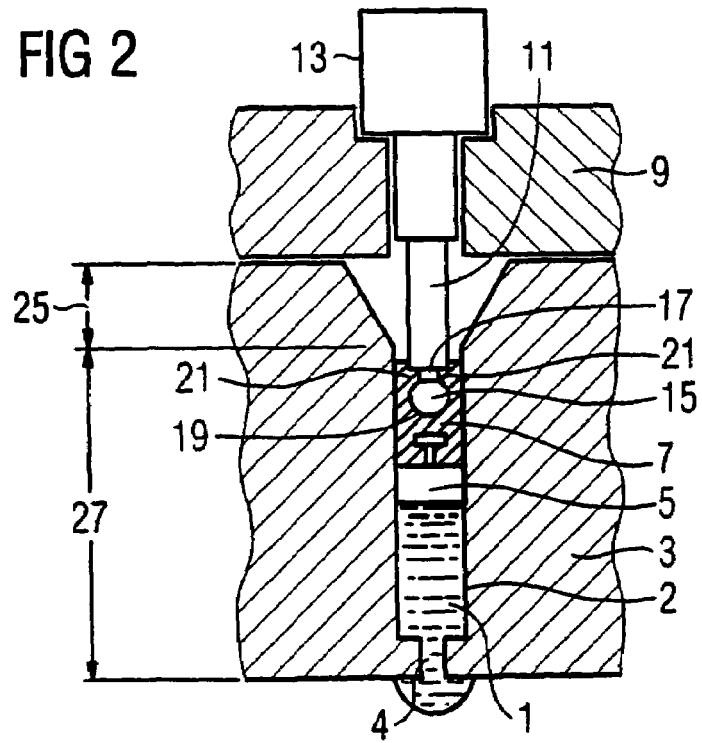

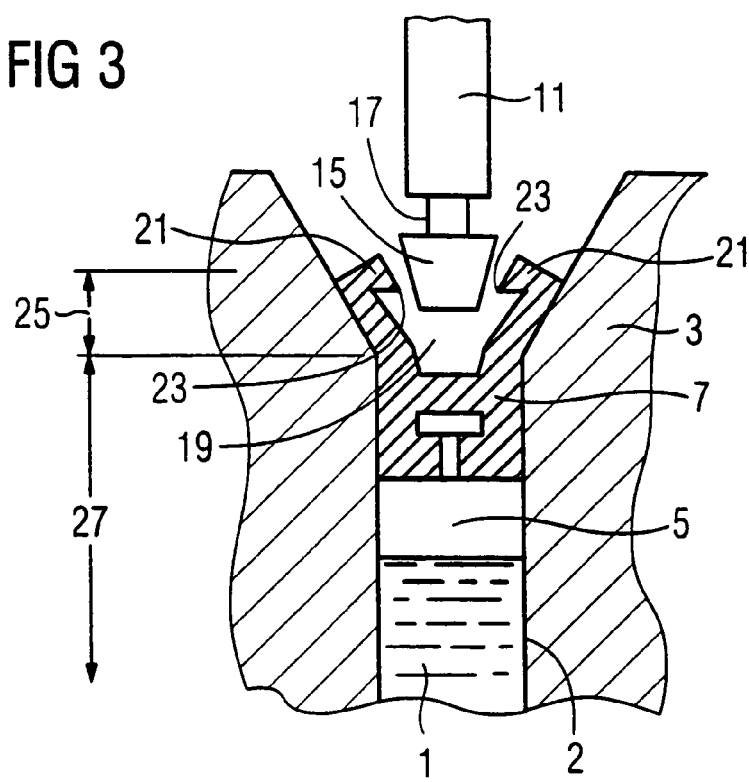
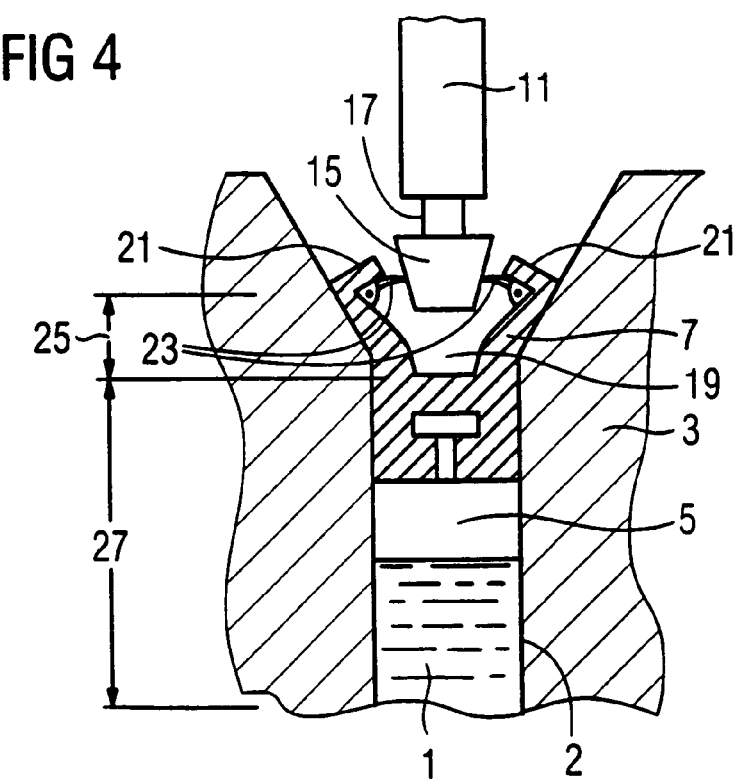

CARTRIDGE WITH CONNECTION FOR A PUMP-DRIVE AND FLUID HANDLING SYSTEM

BACKGROUND OF THE INVENTION

1. Field of the Invention

The present invention concerns a cartridge for handling and transport of a fluid (liquid or gaseous substance), as well as a system for handling a fluid using such a cartridge. The invention concerns in particular a cartridge for handling a medical fluid as well as an analysis device to examine medically relevant properties of a fluid using such a cartridge.

2. Description of the Prior Art

In medical diagnostics, a number of examinations are implemented on liquids or gases (fluids), for example blood, urine, saliva, gastric juices, or respiratory air. The examinations can provide the analysis of widely varied parameters of chemical, microbiological, or physical properties. In addition to the ascertainment of measurements such as the pH value, the content of particular chemical elements or compounds, or the determination of the bacteria count, microbiological analysis methods play an increasingly larger role. These frequently have as a goal the electrochemical detection of nucleotide sequences that can indicate genetic aberrations or the existence of pathogenic bacteria or viruses. The detection of nucleotide bases is normally based on a two-stage method, in the first step of which DNA fragments present in the fluid are reproduced multiple times, in order to increase the probability of detection for the actual detection in the second step. Since genetic contamination is also thereby multiplied, this method poses particularly high demands on the cleanliness of the procedural apparatuses.

The analysis of fluids also plays a large role in chemical and biochemical analysis techniques. Such methods can be of great importance in chemical laboratories, in industry, in environmental protection, or the production of food. Depending on the field of application, particular requirements can be made on the purity of receptacles for the implementation of the analysis method.

In addition to handling for the purpose of examination (wherein handling is primarily understood as dosing), the handling of fluids also can be necessary with regard to industrial or food industrial applications, where frequently it means storage and transport first. In particular in large industrial application measures, immense numbers of handling events can ensue for individual liquid or gas quantities.

While the handling of fluids under everyday conditions poses no particular problem, high numbers of handling events or high requirements of a particular degree of purity entail substantially large financial and handling-technical expenditure. The need for extreme cleanliness of the receptacles requires a number of individual cleaning steps with correspondingly high labor expenditure. The handling and dosing of fluids in large numbers of handling events and high numbers of individual quantity units can be achieved only with a high degree of technical automation of the devices involved.

If high requirements as to purity and handling coincide with high handling high numbers of units, the one-time use of the equipment has heretofore been uneconomical, and in addition the need for a large personnel staff is inevitable, due to the high price of the complex devices for handling and for cleaning. Even when it is only large numbers of handling events that occur, a significant handling burden already exists that cannot be maintained. For example, even a modest reduction in the number of handling steps that are serially implemented in a central medical or chemical analysis laboratory for a number of small customers, or the large measures in a chemical or food industrial production, leads to savings of labor and time in significant amounts.

The large number of handling events with discrete fluid quantities can be implemented with a large number of substance containers, also called cartridges. A disadvantage, however, is that the cartridges must be individually handled in similarly large numbers, and devices provided for this use must be installed. Particular requirements as to logistics or cleanliness can be fulfilled with a large number of cartridges, if these are sufficiently advantageous that they can be economically used as one-time products. Here there is the additional problem that, in spite of advantageous costs, handling expenditure should be minimized.

SUMMARY OF THE INVENTION

An object of the present invention is to enable the handling of a fluid in cartridges with only a minimal handling effort, but which is sufficiently economically feasible for single (one-time) use products.

The above object is achieved in accordance with the invention in a cartridge for a fluid, as well as a system for handling a fluid using such a cartridge, wherein the cartridge has a tank shaped as a cylinder with an opening to admit and discharge the fluid, as well as a piston that can be moved forward and/or back in the tank in order to pump the fluid in or out through the opening. The piston has a connection element that can be connected with an actuator in order to move the piston forward and/or back. The connection element and the actuator are adapted to one another such that the connection is automatically closed in a first longitudinal section of the tank, given movement of the piston in the longitudinal direction, and is automatically released again given movement in the opposite direction. The connection remains closed in a second longitudinal section of the tank, given movement of the piston into this second longitudinal section.

The invention is based on the use of a cartridge that possesses an integral pump system actuated from outside the cartridge to handle fluids. As used herein, the term cartridge means a substance container, adapted to particular requirements, that can have thick or thin walls and may have additional features such as integrated heating or cooling systems or the like. The pump system, for example a pump piston, can automatically couple and decouple with the pump actuation of a handling system by means of a positive-fit connection. It is thus not necessary to use additional pump systems such as, for example, injectors or piston pumps for handling. In the handling, additional effort for the coupling and decoupling of the cartridge to the handling system thus can be avoided.

In the invention the pump system, in addition to the cartridge, is also manufacturable from inexpensive components such as molded plastic components. The cartridge thus can be manufactured at a low cost and made available in large quantities. The ability to economically manufacture large quantities is of particular advantage in the use of the cartridge for central, serial laboratory examination of large numbers of probes that must be spatially separately removed on site. The low-cost manufacturability of the cartridges in large numbers makes them economically useable in addition as a one-time product. Additionally, the logistic effort for frequent, spatially separate use can thereby be reduced. Time and expense for the complex cleaning of the cartridges is not needed with regard to analysis methods that have particular requirements as to purity. In spite of this, the cartridges not yet contaminated in the manufacture are sterilized or cleaned according to requirements and subsequently packed sealed, for example in a blister pack, as is typical for medical products. The substantially complicated cleaning of already used, thus contaminated cartridges can then be completely dispensed with.

In an embodiment of the invention, the production outlay is minimized by designing the automatically producible connection between integral pump system of the cartridge and the pump actuator of the analysis device or dosing device without complicated, fine mechanical working parts, and solely on the basis of an elastic, formed component. The elastic, formed component is fashioned such that has catches or jaw elements that, upon infeed of the integral pump system via the external pump actuator, enters into a positive-fit connection by means of a longitudinal motion. The positive-fit connection allows the integral pump system also to be retracted by the pump actuator, with the positive-fit connection becoming detached when, upon the retraction, the integral pump system once again reaches its starting point.

A further advantage is that the integrated pump system is implemented as a one-time use system. It can, if necessary, undergo the same cleaning steps as the entire cartridge, and therefore fulfills the same requirements for purity. In the one-time use, it must likewise not be elaborately cleaned for reuse. Moreover, the purity of the fluids to be handled also benefits from the integration of the pump system, because the transfer via and the contact with additional pump systems, for example injectors, is avoided.

A further object of the invention is to provide a system that enables the handling of fluids by means of a low-cost producible cartridge that can be automatically coupled and again decoupled with the system via a positive-fit connection. Due to the automatic coupling, the number of individual handling steps is reduced. The low-cost manufacturability of the cartridges enables the economic application in large quantities and use as a one-time product.

DESCRIPTION OF THE DRAWINGS

FIG. 1 shows a cartridge and analysis device or dosing device with a disconnected pump actuation in accordance with the invention.

FIG. 2 shows cartridge and analysis device or dosing device with a connected pump actuation in accordance with the invention.

FIG. 3 is an enlarged depiction of an embodiment of the connection components.

FIG. 4 is an enlarged depiction of a further embodiment of the connection components.

DESCRIPTION OF THE PREFERRED EMBODIMENTS

FIG. 1 shows a system according to the invention with a cartridge 3 and a dosing device or analysis device 9. The cartridge 3 can be formed of plastic, metal or another suitable material, dependent on the liquid or the gas to be handled. The cartridge 3 has a tank 2 shaped as a cylinder, the cross-section of which can be arbitrarily fashioned, but the simpler shapes are semi-circular and circular. Located in the tank 2 in FIG. 1 is a fluid 1 that is pumped in via an opening 4 lying the front wall of the tank 2. A piston 5 is arranged in the tank 2 that can be moved forward and back in order to pump the fluid in or out. So that the pump 5 can form a sealed connection with the inner wall of the tank 2, the surfaces on both sides have a suitable surface finish. Moreover, at least one of the two sealing components can be made of elastic material. To satisfy the requirement for impermeability, if needed, seal rings can be arranged on the piston 5 (which are not shown in FIG. 1).

The piston 5 has a connection element 7 that is shown in FIG. 1 as a separate component mechanically connected with the piston 5. However, it is also possible to integrally produce the piston 5 and connection element 7, i.e. as a single component that can decrease of the production outlay. Non-integrated components may be necessary in the event that the fluid 1 contacting the piston 5 has properties that require the use of material for the piston 5 that is incompatible with the mechanical requirements for the material of the connection element 7. For example, the connection element 7 could be made of elastic plastic, however the fluid 1 may exhibit aggressive characteristics with regard to the plastic. In this case, the piston 5 cannot be fashioned from plastic, but rather must be formed, for example, of metal.

The piston 5 can be detected by the dosing or analysis pump device 9 via a piston rod 11 that is actuated by an actuator 13. If the piston rod 11 is moved forward by the actuator 13, it can move the piston 5 via the connection element 7 deeper into the tank 2. Fluid 1 is thereby pumped out via the opening 4. The dosing or analysis pump device 9 controls the actuator 13 and can thus exactly dose the quantity of fluid 1 that leaves via the opening 4. Due to the linear movement of the piston rod 11 and the consistent cross-section of the tank 2, the existing volume is directly dependent on the movement of the piston rod 11, whereby under the circumstances the elasticity of the piston 5 or the connection element 7 must be considered.

Moreover, the invention enables the piston 5 to be retracted by retracting the piston rod 11, and thereby to pump fluid 1 into the tank 2 via the opening 4. For this purpose, the opening 4 can be fashioned either as a nozzle to accept fluid 1, in direct contact with the fluid 1 to be pumped in, or it can be a nozzle or needle that can be placed at the opening 4. In the event that the opening 4 is not in direct contact with fluid and the piston is retracted, surrounding air is pumped into the tank 2 in place of fluid 1.

So that the piston 5 can be retracted via the piston rod 11, the connection element 7 and the end of the piston rod 11 are fashioned such that a positive-fit connection with regard to mutual, longitudinal motion can be produced between them. In order to be able to produce this positive-fit connection, the connection element 7 has a connection bushing 19 that is formed by a depression in the end of the connection element 7 opposite the piston 5. The wall of the connection element 7, in the area of this depression, has catch elements 21 that are implemented in FIG. 1 as semicircular jaws. In contrast, the piston rod 11, has at its end facing the connection element 7, has a connection plunger 15 that is terminated by a tapering 17.

The connection bushing 19 and the connection plunger 15 are formed such that, given movement of the piston rod 11, they can enlarge in order to automatically close the connection. For this purpose, the cross-section of the tank 2 expands to the end in the section in which the connection element 7 lies. This expansion enables it to avoid catching mechanisms 21 on the way out, due to the elasticity of the connection element 7 from the connection plunger 15. The connection between the piston rod 11 and the piston 5 in FIG. 1 is therefore not closed.

The cartridge 3 and the piston 5, as well as the connection element 7, have a comparatively simple assembly that allows economic production and assembly as a one-time product.

FIG. 2, the same system as in the preceding Figure is shown, however here with a closed connection between the piston 5 and the piston rod 11. The piston rod 11 was moved far enough by the actuator 13 to engage the connection bushing 19 of the connection element 7. The piston 5 was thereby moved over the connection element 7 so far that the catch elements 21 in FIG. 2 no longer lie in the expanded section of the tank 2, but rather are moved into the cylindrical part. Given movement of the catch elements 21 through the tapered section of the tank 2, they are increasingly pressed in the direction of the connection plunger 15 until they are completely pressed in the cylindrical section of the tank 2. The catch elements 21 are thereby pressed into the tapering 17 of the piston rod 11, and the connection plunger 15 completely fills the connection bushing 19. For this purpose, the depth of the connection bushing 10 and the arrangement of the catch elements 21 in the bushing correspond exactly to the length of the connection plunger 15 and the laterally reversed inverted arrangement of the tapering 17.

It can be seen in FIG. 2 that the catch elements 21 engage in the tapering 17 such that, with regard to lengthwise motion, a positive-fit connection is formed. This means that the piston 5 can be moved precisely forward and back by moving the piston rod 11. Both the pumping in and the pumping out of fluid 1 are thereby possible through opening 4.

The positive-fit connection between the connection plunger 15 and the connection bushing 19 is automatically produced by the particular shape of the tank 2. For this purpose, the connection element 7 must be produced from an elastic material, such that the catch elements 21 slant outwardly without interaction of an external force by the connection plunger 15. Due to this elastic force, they automatically assume the position shown in FIG. 1, in which the positive-fit connection is not shown. Given retraction of the piston rod 11, the connection to the connection element 7 again automatically loosens as soon as the catch elements 21 exit from the cylindrical section of the tank 2 in the expanded section. The positive-fit connection thus can be closed automatically and again later automatically released, subject only to the control of the piston rod 11 via the dosing or analysis pump device 9.

The automatic production of the connection between the piston rod 11 and the piston 5 in particular enables the cartridge to connect without complexity with the dosing or analysis pump device 9. It can easily be operate by untrained personnel, since the actual functional connection to the control of the pump event is automatically produced. It is thus not dependent on the precision with which the cartridge is manually applied to the dosing or analysis pump device 9. This increases on the one hand the precision in the dosing of small amounts of fluid 1 via the dosing or analysis pump device 9, and enables the installation and de-installation of the cartridge 3 with minimal effort, in particular in the frequent handling of large quantities.

The described system thus has the ability to implement centralized, in particular stationary, analyses using one-time cartridges in large quantities. Furthermore, the cartridge 3 can be produced as a one-time cartridge with the desired degree of purity, in order to also enable an application in purity-critical analyses as are implemented in microbiology, chemistry or medicine. Large numbers of discrete substance quantities are also possible in food production, the chemical industry, or other industrial applications.

The connection element 7 and the connection plunger 15 are shown enlarged in FIG. 3 in another embodiment. In particular, given use of elastic materials for the production of the connection element 7, or given use of foil joints for the molding of the connection bushing 19, the problem can occur that the piston 5 may not be removed sufficiently far by the piston rod 11. This therefore causes the catch elements 21 to elastically replace upon retracting the connection plunger 15. Upon retraction of the connection plunger 15, the catch elements are thereby pulled in a more strongly expanded section of the tank 2, then released, but then elastically shorten and move to a strongly tapered section. If the connection plunger 15 is subsequently moved again, it impacts the catch elements 21 in the strongly tapered section of the tank 2; the catch elements 21 then are too close to one another, and the connection plunger 15 can not be inserted into the connection bushing 19 again. A consequence of that would be that no positive-fit connection is produced between piston rod 11 and piston 5, and the piston 5 could subsequently no longer be retracted after further movement.

In order to prevent this, the catch elements 21 in FIG. 3 exhibit a shape that is less easily elastically deformable in the direction of retraction than in the direction of motion. Ideally, they are not elastic at all in the direction of retraction, but rather remain rigid in their position. The connection plunger 15 can be inserted more easily into the connection bushing 19 than extracted. In order to achieve this, the catch elements 21 are shown as saw tooth-like tines that "grasp" in the tapering 7, but they can be gently pressed to the side at their flat side given movement of the piston rod 11. In order to facilitate the engagement of the catch elements 21 in the tapering 7 in the direction of retraction, the connection plunger 15 exhibits a flat back on which the catch elements 21 are placed, without sliding laterally. The tapering 7 and the connection plunger 15 and catch elements 21 interact as a toothed catch.

A further variant of the connection element 7 is shown in FIG. 4 in enlarged depiction. The variant shown in FIG. 4 has the same goal as the variant shown in FIG. 3, namely to prevent the premature release of the connection element 7 in the direction of retraction. As a supplement to the elastic catch elements 21, here additional mechanical catches 23 are provided. These are attached such that they can be folded to the side in the direction of insertion of the piston rod 11, however in the opposite direction are prevented by stops from folding away. Upon movement in the connection bushing 19, the connection plunger 15 can press the catches to the side, without the a movement force would thereby be exerted on the piston 5. The catches 23 are applied such that they engage in the tapering 7 as soon as the connection plunger 15 is completely inserted in the connection bushing. For this purpose, the catches 23 must be pressed back by spring force or an elastic suspension into their original position shown in FIG. 4.

The catches 23 ensure a secure positive-fit connection between the connection element 7 and the piston rod 11 that can not release prematurely given retraction, since the catches 23 can not be folded away in the direction of retraction. They are not made of elastic material, but produced from rigid materials, for example from hard plastic or metal. In contrast to this, the connection element 7 is formed of elastic material in order to be able to force the catch elements 21 into their original position, or in addition can have a pre-stressed spring mechanism (not closely shown in FIG. 4).

In a further (not shown) variant of the connection element 7, it is not made of elastic material, but rather of a hard material such as hard plastic or metal. In this variant, the automatic production of the connection between piston 5 and piston rod 11 must be ensured by an expanded functionality of the catches 23. While the catch elements 21, and thus the catches 23, could be pressed (in the preceding specified variant, by the expansion of the tank 2) sufficiently far away from the connection plunger 15 in order to release the connection upon retraction, this possibility is lost given use of a non-elastic connection element 7. It is therefore not necessary to fashion the end area of the tank 2 with a continually expanding cross section. Instead, the connection element 7 is likewise shaped cylindrically, like the piston 5, i.e. with a constant diameter over its length.

In order to ensure the necessary functionality of the catches 23, they have in the variant not shown a locking device that blocks their movement in the direction in which they release the connection plunger 15. In the other direction, their movement is not limited, such that the connection plunger 15 can be inserted into the connection bushing 19 unhindered at any time. The locking device that blocks the movement of the catches 23 can be implemented, for example, as a toothed catch that, upon retraction of the connection element 7, is released at a predetermined longitudinal section of the tank 2. Although such a variant with mechanically moveable catches 23 would bring with it a significantly greater production outlay, a reliable connection and a greater precision in the dosing of fluid to be pumped into the tank 2 can be achieved.

Independent from the respective pump mechanism or connection mechanism, the cartridge 3 and the dosing or analysis pump device 9 can be correspondingly fashioned respectively according to individual requirements. Instead of an elaborately controlled automatic apparatus, the pump device 9 can thus also be a manually controlled device that, for example, provides the removal of blood protein directly into the cartridge 3 in the framework of medical examinations. The actuator 13 would then be provided with a sterile intravenous needle. When, instead of blood tests, for example water tests for environmental technical or chemical examinations should be taken, such an apparatus could be used that would then have a nozzle instead of a needle at the opening 4 of the cartridge. In an industrial large-series application high-volume application, the automatically producible and releasable connection between cartridge 3 and pump device 9 could be used in order to fill or empty a plurality of cartridges 3 in rapid sequence via the pump device. According to the application, the cartridges 9 can be mechanically stable, cushioned against vibrations, able to be cooled, able to be heated, easily transportable due to their shape, or fashioned in a high-volume system such that they can be integrated. Furthermore, the opening 4 and the piston 5 can be sealed in order to prevent unintentional leaking of fluid 1.

Although modifications and changes may be suggested by those skilled in the art, it is the intention of the inventor to embody within the patent warranted hereon all changes and modifications as reasonably and properly come within the scope of his contribution to the art.

I claim as my invention:

1. A cartridge for a fluid comprising:

a cylindrical tank having an opening that admits and discharges fluid relative to the tank, said tank having a first longitudinal section and a second longitudinal section adjoining said first longitudinal section;

a piston movable in a longitudinal direction toward and away from said opening to pump a fluid through the opening into or out of the tank;

a connection element that engages an actuator for moving said piston in said longitudinal direction, said connection element that mechanically interacts with said actuator to produce a positive fit therewith, said connection element being movable back and forth between said first and second longitudinal sections of said tank so as to be alternatingly disposed in and engaging said first longitudinal section and disposed in and engaging said second longitudinal section; and said second longitudinal section having a shape that forces said connection element to interact with said actuator to produce said positive fit when said connection element is in said second longitudinal section and said first longitudinal section having a shape that automatically releases said positive fit when said connection element is in said first longitudinal section.

2. A cartridge as claimed in claim 1 wherein said connection element comprises a connection bushing, and wherein said actuator comprises a connection plunger, said connection bushing and said connection plunger interacting with each other to produce said positive fit when said connection element is in said second longitudinal section.

3. A cartridge as claimed in claim 1 wherein said connection element comprises a catch element and wherein said actuator has a tapering, said catch element engaging said tapering when said connection element is in said second longitudinal section.

4. A cartridge as claimed in claim 1 wherein said tank has a longitudinally open end at a side thereof opposite said opening, and wherein said first longitudinal section conically expands toward said open end.

5. A cartridge as claimed in claim 4 wherein said connection element comprises a catch element and wherein said actuator comprises a tapering, said catch element being permitted by said conically expanding first section to remain out of engagement with said tapering as long as said catch element is at least partially in said first longitudinal section, and said catch element being pressed against said tapering as said connection element is moved in said longitudinal direction into said second longitudinal section.

6. A cartridge as claimed in claim 1 wherein said connection element comprises a catch element and wherein said actuator comprises a tapering engageable with said catch element, said catch element being an elastic catch that, upon movement of said actuator in said longitudinal direction, comes into contact with said actuator at a first point and, upon further movement in said longitudinal direction of said actuator, is elastically pushed away, and first engages said tapering at a second point of said longitudinal movement and, given further movement of said actuator in an opposite direction, remains rigid in said tapering until again reaching said first point.

7. A cartridge as claimed in claim 1 wherein said tank is adapted for handling a medical liquid for examination.

8. A system for handling a fluid, comprising:

a cartridge having a cylindrical tank having an opening to admit and discharge a fluid, said tank having a first longitudinal section and a second longitudinal section adjacent to said first longitudinal section;

a piston movable in a longitudinal direction in said tank toward and away from said opening to pump the fluid into and out of the opening;

a pump device having an actuator engageable with the piston to move the piston in said longitudinal direction; and said piston having a connection element that interacts with said actuator to move said connection element back and forth between said first longitudinal section and said second longitudinal section so as to be alternatingly disposed in and engaging said first longitudinal section and disposed in and engaging said second longitudinal section, said second longitudinal section having a shape that forces said connection element producing a mechanically positive fit with said actuator when said connection element is in said second longitudinal section of said tank, and said first longitudinal section having a shape that automatically releases said actuator from said connection element when said connection element is in said first longitudinal section of said tank.

9. A system as claimed in claim 8 wherein said cartridge is adapted for handling a medical fluid to be examined.

10. A system as claimed in claim 8 wherein said pump device is adapted to implement a medical examination of the fluid.

11. A cartridge as claims in claim 1 wherein said connection element has a spherically-shaped receptacle adapted to receive a free end of said actuator.

12. A system as claimed in claim 8 wherein said actuator has a spherically-shaped free end, and wherein said connection element has a spherically-shaped receptacle therein that forms said positive fit when said actuator when said connection element is in said first longitudinal section of said tank.

13. A system as claimed in claim 8 wherein said actuator has a tapering free end, and wherein said connection element has a tapering receptacle therein that forms said positive fit when said actuator when said connection element is in said first longitudinal section of said tank.

* * * * *